United States Patent
Utsunomiya et al.

(10) Patent No.: US 10,251,626 B2
(45) Date of Patent: Apr. 9, 2019

(54) MEDICAL IMAGE PROCESSING APPARATUS AND NON-TRANSITORY COMPUTER-READABLE STORAGE MEDIUM

(71) Applicant: Toshiba Medical Systems Corporation, Otawara-shi (JP)

(72) Inventors: Kazuki Utsunomiya, Nasushiobara (JP); Yusuke Kano, Nasushiobara (JP); Shinya Sugiyama, Nasushiobara (JP); Kei Mori, Shioya (JP); Tooru Kato, Nasushiobara (JP); Hiroaki Nakai, Nasushiobara (JP)

(73) Assignee: Toshiba Medical Systems Corporation, Otawara-shi (JP)

( * ) Notice: Subject to any disclaimer, the term of this patent is extended or adjusted under 35 U.S.C. 154(b) by 185 days.

(21) Appl. No.: 15/470,256

(22) Filed: Mar. 27, 2017

(65) Prior Publication Data

US 2017/0290569 A1 Oct. 12, 2017

(30) Foreign Application Priority Data

Apr. 11, 2016 (JP) ................................ 2016-079140

(51) Int. Cl.
*A61B 8/00* (2006.01)
*A61B 8/08* (2006.01)
(Continued)

(52) U.S. Cl.
CPC .............. *A61B 8/463* (2013.01); *A61B 8/085* (2013.01); *A61B 8/0825* (2013.01); *A61B 8/14* (2013.01);
(Continued)

(58) Field of Classification Search
CPC ....... A61B 8/463; A61B 8/0825; A61B 8/085; A61B 8/14; A61B 8/464; A61B 8/465;
(Continued)

(56) References Cited

U.S. PATENT DOCUMENTS

| 2004/0151358 A1* | 8/2004 | Yanagita | ............... G06F 19/321 382/132 |
| 2007/0038085 A1* | 2/2007 | Zhang | .................... A61B 6/463 600/437 |

(Continued)

FOREIGN PATENT DOCUMENTS

JP 2015-27450 2/2015

*Primary Examiner* — Kim Y Vu
*Assistant Examiner* — Molly Delaney
(74) *Attorney, Agent, or Firm* — Oblon, McClelland, Maier & Neutstadt, L.L.P.

(57) ABSTRACT

According to one embodiment, a medical image processing apparatus includes a storage and processing circuitry. The storage stores a first image indicating a breast of an object captured by a medical image diagnostic apparatus and interpretation information associated with the first image. The processing circuitry generates, based on position information of a region of interest based on the interpretation information and information of an interpretation direction, schematic diagram information for adding information about a position of the region of interest onto a schematic diagram of the breast. The processing circuitry transmits information, including the schematic diagram information, for generating the schematic diagram.

21 Claims, 14 Drawing Sheets

(51) Int. Cl.
*A61B 8/14* (2006.01)
*G06F 19/00* (2018.01)

(52) U.S. Cl.
CPC .............. *A61B 8/464* (2013.01); *A61B 8/465* (2013.01); *A61B 8/466* (2013.01); *A61B 8/467* (2013.01); *A61B 8/469* (2013.01); *A61B 8/488* (2013.01); *A61B 8/565* (2013.01); *G06F 19/00* (2013.01); *A61B 8/406* (2013.01); *A61B 8/4427* (2013.01); *A61B 8/4477* (2013.01)

(58) Field of Classification Search
CPC ......... A61B 8/466; A61B 8/467; A61B 8/469; A61B 8/488; A61B 8/565; G06F 19/00
See application file for complete search history.

(56) References Cited

U.S. PATENT DOCUMENTS

| | | | | |
|---|---|---|---|---|
| 2011/0144482 | A1* | 6/2011 | Sendai | G06T 7/0012 600/425 |
| 2012/0014578 | A1* | 1/2012 | Karssemeijer | G06T 7/0012 382/131 |
| 2014/0082542 | A1* | 3/2014 | Zhang | G06F 19/321 715/771 |
| 2015/0279064 | A1* | 10/2015 | Dennerlein | G09G 5/02 382/131 |
| 2016/0110875 | A1* | 4/2016 | Sugiyama | A61B 8/0825 382/131 |
| 2017/0086791 | A1* | 3/2017 | Chae | A61B 5/00 |
| 2017/0128037 | A1* | 5/2017 | Mori | A61B 8/0825 |
| 2018/0055479 | A1* | 3/2018 | Lalena | G01S 7/52098 |

* cited by examiner

| Transmission destination | Screen size | Transmission method | Transmission rate [Mbps] |
|---|---|---|---|
| High-definition monitor | 2048×2560 | TCP/IP | 25 |
| UL apparatus (full screen) | 1280×1024 | TCP/IP | 20 |
| UL apparatus (2 screens (vertical)) | 640×1024 | USB memory | 5 |
| UL apparatus (2 screens (horizontal)) | 1280×512 | Bluetooth | 0.5 |
| UL apparatus (second monitor) | 1024×768 | CD | 0.3 |
| Tablet (12-inch, landscape) | 2160×1440 | TCP/IP (wireless) | 2 |
| Tablet (8-inch, landscape) | 1920×1200 | NFC | 0.8 |
| Report output | 1024×768 | USB cable | 150 |
| ... | | | |

| Transmission destination | Screen size | Transmission method | Transmission rate [Mbps] |
|---|---|---|---|
| UL apparatus (full screen) | 1280×1024 | TCP/IP | 20 |

FIG. 8B

| Interpretation ID | Image ID CC/MLO | Region of interest (ROI) Coordinates : Size | Finding comment |
|---|---|---|---|
| R0001 | 1001 | (124,45):10 | Presence of calcification in inside upper portion of right breast |
| | 1002 | (253,75):13 | |

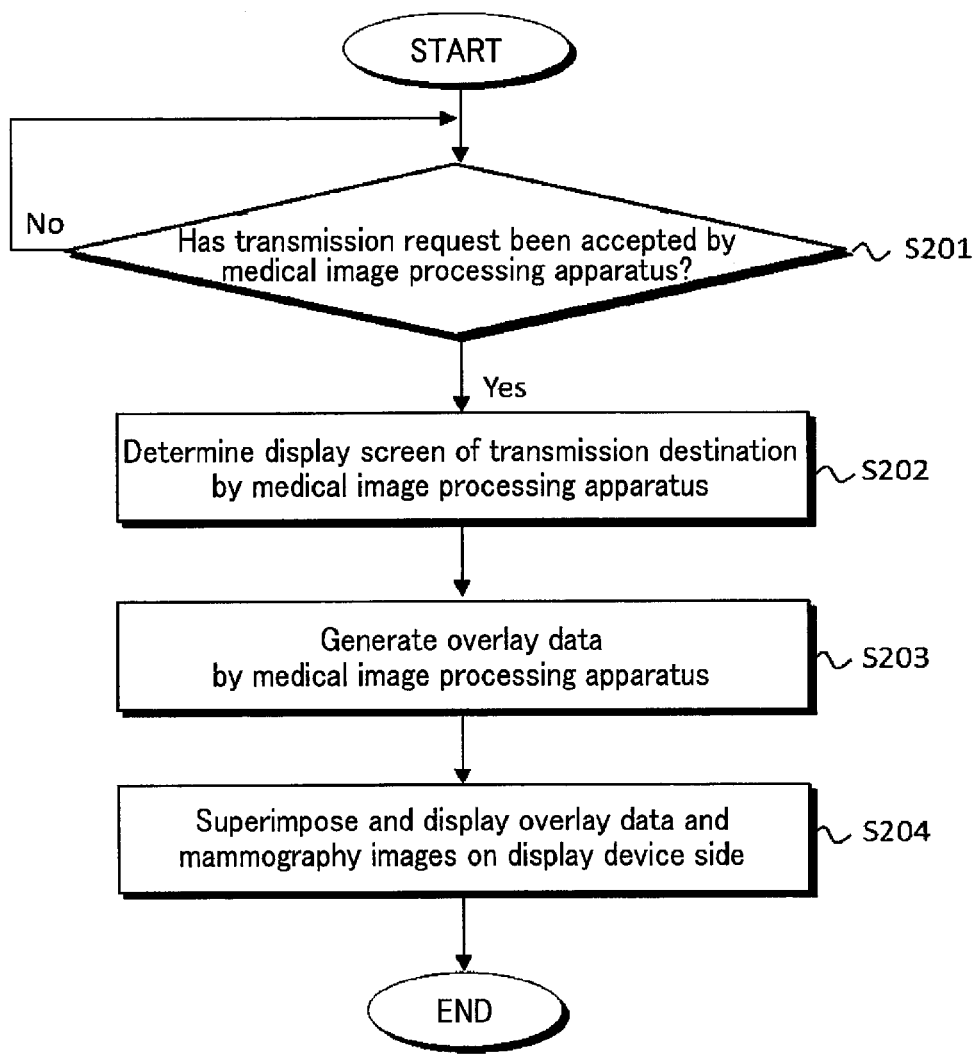
F I G. 13

MEDICAL IMAGE PROCESSING APPARATUS AND NON-TRANSITORY COMPUTER-READABLE STORAGE MEDIUM

CROSS-REFERENCE TO RELATED APPLICATIONS

This application is based upon and claims the benefit of priority from the prior Japanese Patent Application No. 2016-079140, filed Apr. 11, 2016, the entire contents of which are incorporated herein by reference.

FIELD

Embodiments described herein relate generally to a medical image processing apparatus and a non-transitory computer-readable storage medium comprising a program used by a computer.

BACKGROUND

Conventionally, mammary gland image diagnosis performed in breast cancer screening is generally performed using mammography images captured by a mammography apparatus. To the contrary, in recent years, mammary gland image diagnosis is performed using mammography images and ultrasonic images.

At the time of mammary gland image diagnosis using mammography images and ultrasonic images, in many cases, the first operator captures mammography images, and the second operator captures ultrasonic images with reference to the mammography images. The first operator sets regions of interest on the captured mammography images. A schematic diagram schematically representing breasts is generated using the pieces of position information of the regions of interest on the mammography images and pieces of information respectively indicating the imaging directions of the mammography images. The schematic diagram is transmitted to a display to be used to perform ultrasonic diagnosis together with the mammography images. The second operator may capture ultrasonic images with reference to various kinds of auxiliary information such as the schematic diagram and a finding comment indicating the interpretation information of the mammography images, and the mammography images.

However, there are various display environments to be referred to by the second operator who uses the ultrasonic diagnostic apparatus. A case in which it is difficult for the second operator to refer to the mammography images and auxiliary information displayed on the display depending on the mammography images and the arrangement and/or size of auxiliary information is also assumed. If the mammography images and auxiliary information are displayed on a display having a small display screen by using the layout of the mammography images and auxiliary information, which has been set for a display having a large display screen, it is assumed to be difficult to refer to the auxiliary information on the display having the small display screen.

To help the second operator, it is necessary to adjust, in accordance with the size and/or shape of the display screen of the transmission destination, the mammography images and the auxiliary information such as the above-described schematic diagram to have a layout which is readily visually perceived by the second operator.

BRIEF DESCRIPTION OF THE DRAWINGS

FIG. 6 is a table showing an example of information recorded in transmission destination information storage according to the embodiment;

FIG. 8A is the first explanatory view for explaining a layout determination function according to the embodiment;

FIG. 8B is the second explanatory view for explaining the layout determination function according to the embodiment;

FIG. 13 is a flowchart for explaining the example of the processing according to the embodiment.

DETAILED DESCRIPTION

In general, according to one embodiment, a medical image processing apparatus includes a storage and processing circuitry. The storage stores a first image indicating a breast of an object captured by a medical image diagnostic apparatus and interpretation information associated with the first image. The processing circuitry generates, based on position information of a region of interest based on the interpretation information and information of an interpretation direction, schematic diagram information for adding information about a position of the region of interest onto a schematic diagram of the breast. The processing circuitry transmits this information, including the schematic diagram information, for generating the schematic diagram.

A medical image processing apparatus, a medical information processing system, and a medical information processing program will be described below with reference to the accompanying drawings.

Embodiment

[Medical Information Processing System]

Figure 1:
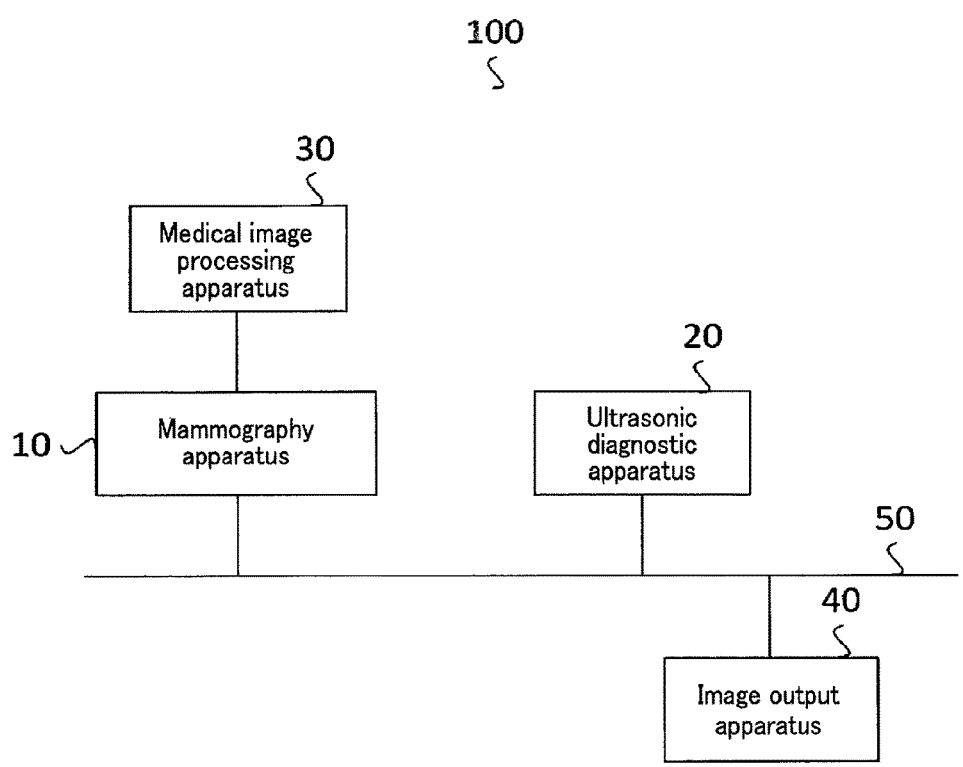
FIG. 1 is a block diagram showing an example of the arrangement of a medical information processing system according to an embodiment.

FIG. 1 is a block diagram showing the arrangement of a medical information processing system 100 according to the embodiment. The medical information processing system 100 according to this embodiment is installed in a hospital where breast cancer screening is performed. The medical information processing system 100 is used at the time of mammary gland image diagnosis using mammography images and ultrasonic images. As shown in FIG. 1, for example, the medical information processing system 100 according to this embodiment includes a mammography apparatus 10, an ultrasonic diagnostic apparatus 20, a medical image processing apparatus 30 connected to the mammography apparatus 10, and an image output apparatus 40. The respective apparatuses are interconnected via a network 50, and mutually transmit/receive image data and the like captured by the mammography apparatus 10 and/or the ultrasonic diagnostic apparatus 20.

Note that in this embodiment, the mammography apparatus 10 and the medical image processing apparatus 30 are connected, and have different arrangements. The present invention, however, is not limited to this. The mammography apparatus 10 may include the function of the medical image processing apparatus 30. Alternatively, as shown in FIG. 1, the mammography apparatus 10 and the medical image processing apparatus 30 are separately formed in a state in which they are connected to each other. If these apparatuses are separately formed, information generated by the medical image processing apparatus 30 connected to the mammography apparatus 10 is transmitted to the ultrasonic diagnostic apparatus 20 and/or the image output apparatus 40 via the mammography apparatus 10. Alternatively, the medical image processing apparatus 30 may be connected to the mammography apparatus 10 not directly but via the network 50.

[Mammography Apparatus]

The mammography apparatus 10 is a form of an X-ray diagnostic apparatus for irradiating a breast of an object with X-rays, detecting X-rays transmitted through the breast, and generating a mammography image (first image).

Figure 2:
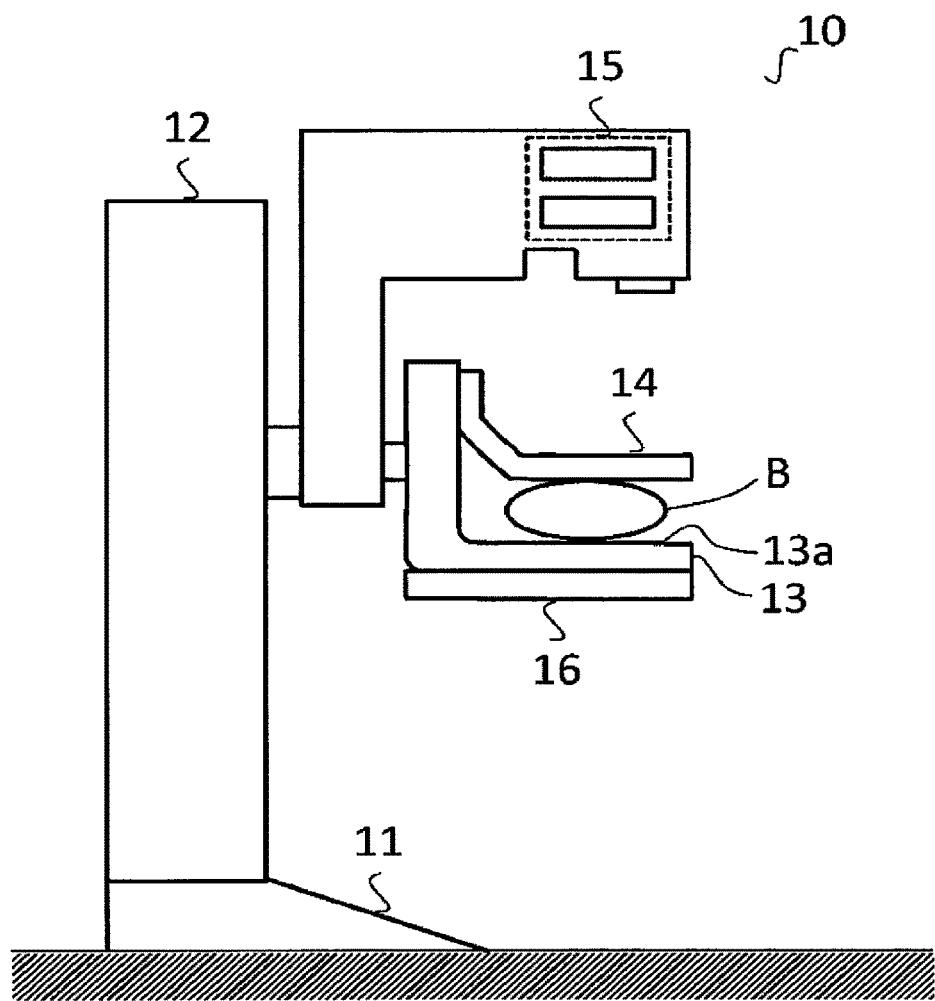
FIG. 2 is a view showing an example of the arrangement of a mammography apparatus according to the embodiment.
Figure 3:
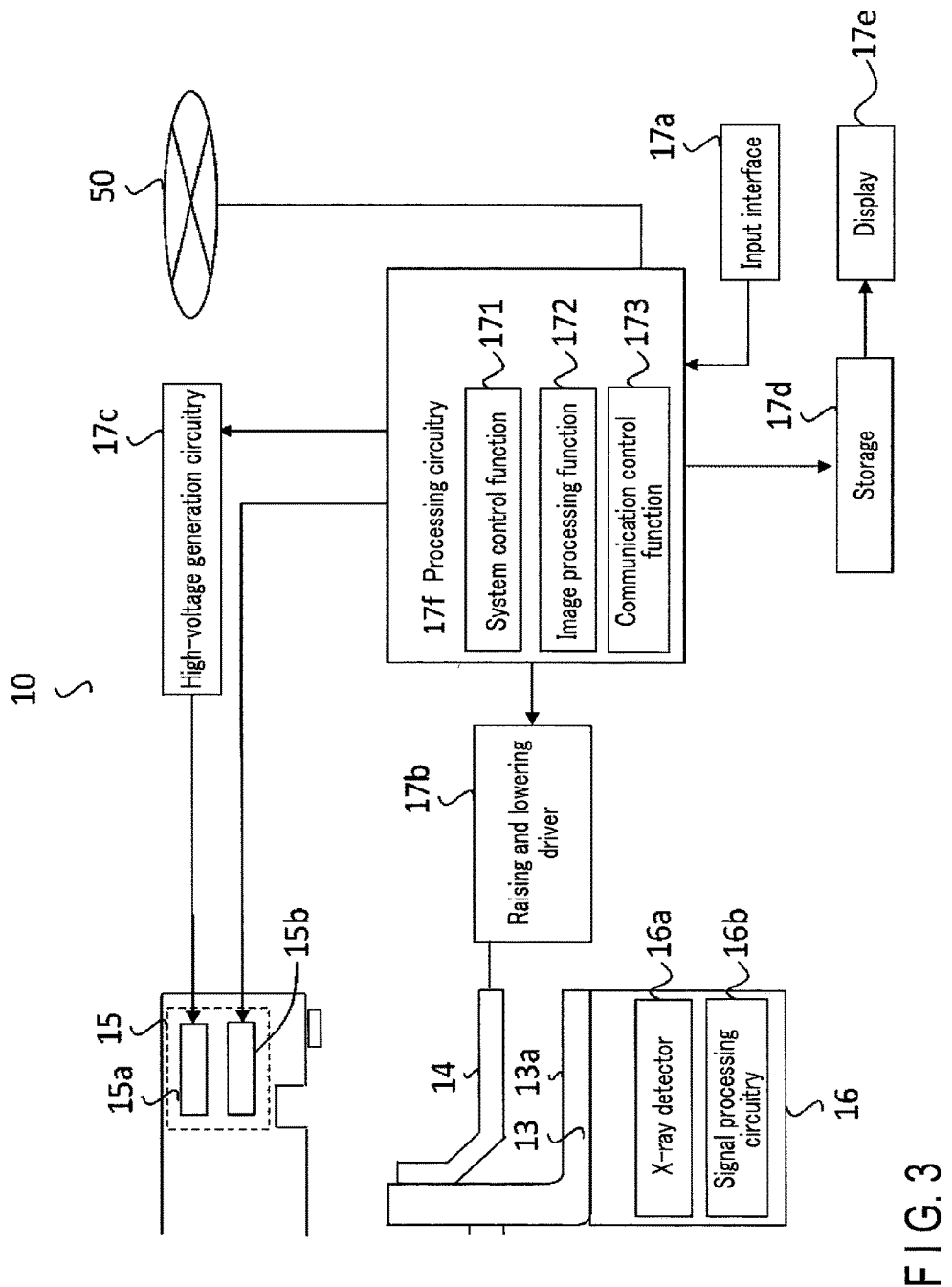
FIG. 3 is a block diagram showing the example of the arrangement of the mammography apparatus according to the embodiment.

FIGS. 2 and 3 are views each showing an example of the arrangement of the mammography apparatus 10 according to the embodiment. For example, as shown in FIG. 2, the mammography apparatus 10 includes a pedestal 11 and a stand 12. The stand 12 stands on the pedestal 11, and supports an imaging stage 13, a pressing plate 14, an X-ray output unit 15, and an X-ray detection device 16. Note that the imaging stage 13, the pressing plate 14, and the X-ray detection device 16 are supported to be movable vertically.

The imaging stage 13 is a stage for supporting a breast B of an object. The imaging stage 13 includes a supporting surface 13a on which the breast B is placed. The pressing plate 14 is arranged above the imaging stage 13. The pressing plate 14 is provided to face the imaging stage 13 parallelly and to be movable in directions to come into contact with and move away from the imaging stage 13. Note that when the pressing plate 14 moves in the direction to come close to the imaging stage 13, it presses the breast B supported on the imaging stage 13. The breast B pressed by the pressing plate 14 is spread, and thus overlapping of mammary glands in the breast B decreases.

As shown in FIG. 3, the mammography apparatus 10 includes an input interface 17a, a raising and lowering driver 17b, high-voltage generation circuitry 17c, a storage 17d, a display 17e, and processing circuitry 17f.

The input interface 17a (input unit) has a function of accepting input operations of various commands and the like from the operator. The input interface 17a includes foot switches and input devices such as a trackball, a joy stick, a main console with various buttons, a keyboard, and a mouse.

The raising and lowering driver 17b is a device including a plurality of motors, gears, and the like. The raising and lowering driver 17b is connected to the imaging stage 13 and the pressing plate 14. The raising and lowering driver 17b has a function of raising and lowering the imaging stage 13 vertically. The raising and lowering driver 17b raises and lowers the pressing plate 14 vertically, that is, in the directions to come into contact with and move away from the imaging stage 13.

The X-ray output unit 15 includes an X-ray tube 15a and an X-ray converging device 15b. The X-ray output unit 15 has a function of outputting X-rays to the object. The X-ray tube 15a is a vacuum tube for generating X-rays. The X-ray tube 15a accelerates thermoelectrons emitted from a cathode (filament) by a high voltage, and makes the accelerated electrons collide against a tungsten anode, thereby generating X-rays. The X-ray converging device 15b is arranged between the X-ray tube 15a and the pressing plate 14. The X-ray converging device 15b is made of lead. The X-ray converging device 15b has a function of controlling the irradiation range of the X-rays generated by the X-ray tube 15a.

The high-voltage generation circuitry 17c is connected to the X-ray tube 15a. The high-voltage generation circuitry 17c is a power supply device for supplying a high voltage to be used by the X-ray tube 15a to generate X-rays.

The X-ray detection device 16 includes an X-ray detector 16a and signal processing circuitry 16b. The X-ray detector 16a has a function of detecting X-rays transmitted through the breast B and the imaging stage 13, and converting the X-rays into an electrical signal (transmitted X-ray data). The X-ray detector 16a comprises, for example, an FPD (Flat Panel Detector). The FPD is formed by two-dimensionally arranging small detection elements in the column and line directions. Each detection element includes a photoelectric film for sensing X-rays and generating charges according to an incident X-ray dose, a charge accumulation capacitor for accumulating the charges generated by the photoelectric film, and a TFT (Thin Film Transistor) for outputting, at a predetermined timing, the charges accumulated in the charge accumulation capacitor.

The signal processing circuitry 16b is electric circuitry for generating X-ray projection data from the electrical signal converted by the X-ray detector 16a.

The storage 17d saves a mammography image generated by an image processing function 172 of the processing circuitry 17f (to be described later). The mammography image generated by the image processing function 172 is displayed on the display 17e. The storage 17d may include, for example, a RAM (Random Access Memory), a semiconductor memory element such as a flash memory, a hard disk, and an optical disk.

The processing circuitry 17f includes a system control function 171, the image processing function 172, and a communication control function 173.

The system control function 171 is connected to the input interface 17a, the raising and lowering driver 17b, the high-voltage generation circuitry 17c, the X-ray converging device 15b, and the processing circuitry 17f. The system control function 171 comprehensively controls the mammography apparatus 10.

The image processing function 172 is connected to the signal processing circuitry 16b and the storage 17d. The image processing function 172 loads the X-ray projection data generated by the signal processing circuitry 16b, and generates a mammography image. The image processing function 172 saves the generated mammography image in the storage 17d. The image processing function 172 is connected to the display 17e. The image processing function 172 displays the generated mammography image on the display 17e.

The display 17e may include a liquid crystal display, a CRT (Cathode Ray Tube) display, a touch panel, or the like. The display 17e displays a GUI (Graphical User Interface) used by the operator of the mammography apparatus 10 to input various instructions and setting requests via the input interface 17a, the mammography image generated by the image processing function 172, and an analysis result.

The communication control function 173 controls communication performed with another apparatus via the network 50. For example, the communication control function 173 transfers, via the network 50, the mammography image generated by the image processing function 172 to the other apparatus. The image transferred via the network 50 can undergo image display, image processing, or the like in the transfer destination apparatus. For example, the communication control function 173 transmits, to the medical image processing apparatus 30 connected to the mammography apparatus 10, the mammography image and information such as a finding comment described by the operator about the mammography image. The communication control function 173 also has a function of transmitting, to the ultrasonic diagnostic apparatus 20 and/or the image output apparatus 40, an overlay image generated by the medical image processing apparatus 30 (to be described later).

Furthermore, each of the processing functions performed by the system control function 171, image processing function 172, and communication control function 173 as the components of the processing circuitry 17f is recorded in the storage 17d in a form of a medical information processing program executable by a computer. The processing circuitry 17f is a processor for implementing a function corresponding to each medical information processing program by reading out the medical information processing program from the storage 17d and executing it. In other words, the processing circuitry 17f which has read out each medical information processing program has each function shown in the processing circuitry 17f of FIG. 3. Note that in FIG. 3, each of the processing functions executed by the system control function 171, image processing function 172, and communication control function 173 is implemented by the single processing circuitry 17f. The present invention, however, is not limited to this. A plurality of independent processors may be combined to form the processing circuitry 17f, and the processors may execute the medical information processing programs to implement the various processing functions.

[Ultrasonic Diagnostic Apparatus]

Referring back to FIG. 1, the ultrasonic diagnostic apparatus 20 collects reflected wave data by scanning the object with an ultrasonic wave using an ultrasonic probe for transmitting/receiving an ultrasonic wave. The ultrasonic diagnostic apparatus 20 generates an ultrasonic image from the collected reflected wave data.

Figure 4:
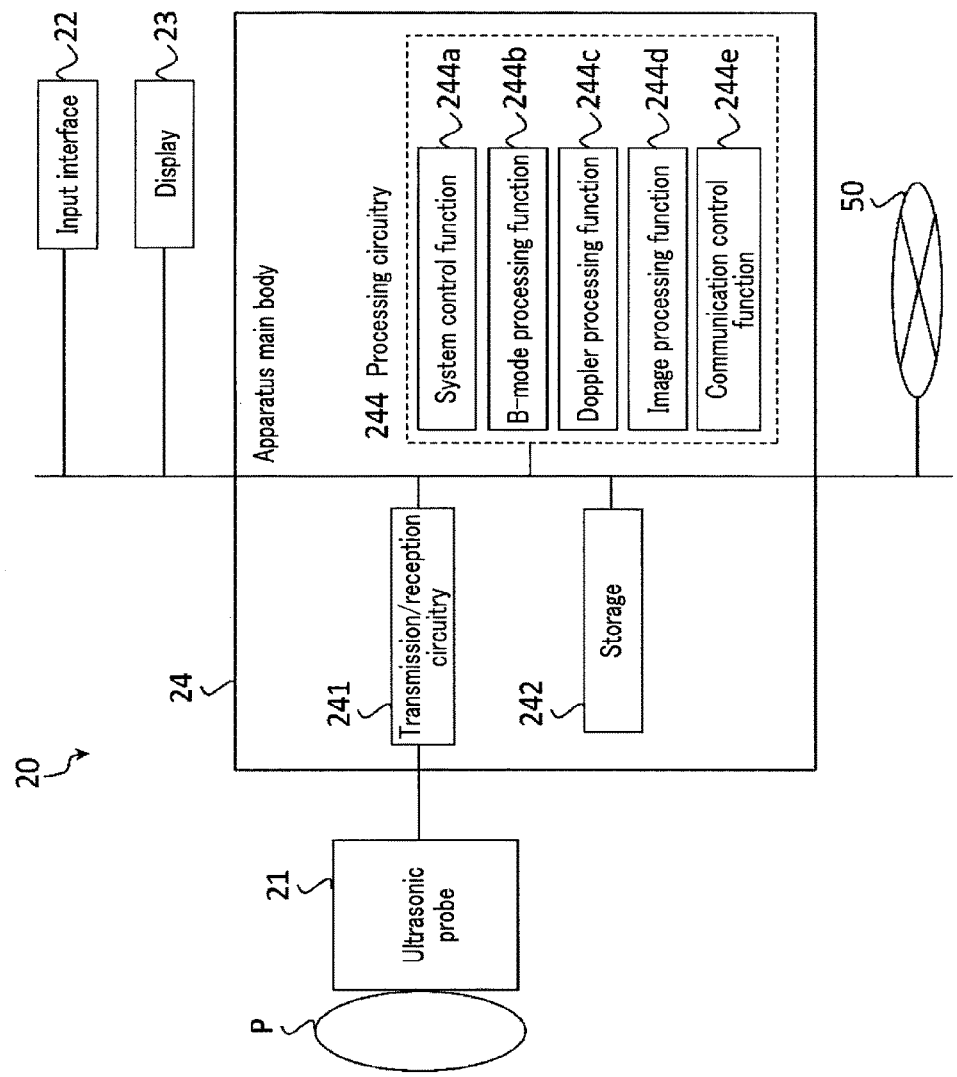
FIG. 4 is a block diagram showing an example of the arrangement of an ultrasonic diagnostic apparatus according to the embodiment.

FIG. 4 is a block diagram showing an example of the arrangement of the ultrasonic diagnostic apparatus 20 according to the embodiment. As shown in FIG. 4, the ultrasonic diagnostic apparatus 20 according to this embodiment includes an ultrasonic probe 21, an input interface 22, a display 23, and an apparatus main body 24.

The ultrasonic probe 21 is formed from a plurality of piezoelectric transducers. Each of the plurality of piezoelectric transducers receives a driving signal supplied from transmission/reception circuitry 241 included in the apparatus main body 24 (to be described later), thereby generating an ultrasonic pulse. Each of the plurality of piezoelectric transducers receives a reflected wave from the object, and converts it into an electrical signal. The ultrasonic probe 21 includes a matching layer provided for the piezoelectric transducers and a backing material for preventing the ultrasonic waves from propagating backward from the piezoelectric transducers.

When the ultrasonic probe 21 transmits ultrasonic pulses to the object, the transmitted ultrasonic pulses are sequentially reflected by a discontinuity surface of acoustic impedance of the living tissue of the object, and received by the plurality of piezoelectric transducers of the ultrasonic probe 21 as an echo signal. The amplitude of the received echo signal depends on an acoustic impedance difference on the discontinuity surface by which the ultrasonic pulses are reflected. Note that the frequency of the echo signal generated when the transmitted ultrasonic pulses are reflected by moving blood or the surface of a cardiac wall or the like shifts depending on the velocity component of the moving body in the ultrasonic transmission direction due to the Doppler effect. If, for example, a tumor portion is recognized in the breast, a blood flow in the tumor portion is conspicuously recognized, as compared with a normal portion. Therefore, it is effective to perform diagnosis using a Doppler image in addition to a B-mode image (to be described later). The B-mode image indicates an image in which the signal intensity of the reflected wave data is expressed by the brightness of luminance. The Doppler image indicates an image generated from data obtained by performing frequency analysis for the velocity information of the reflected wave data, extracting blood, tissue, and a contrast medium echo component by the Doppler effect, and extracting moving body information such as mean velocities, variances, and powers at multiple points.

The input interface 22 may include a mouse, a keyboard, buttons, panel switches, a touch command screen, foot switches, a trackball, and the like, and is connected to the apparatus main body 24. Furthermore, the input interface 22 accepts various instructions and setting requests from the operator of the ultrasonic diagnostic apparatus 20, and transfers the accepted various instructions and setting requests to the apparatus main body 24.

The display 23 may include a liquid crystal display, a CRT display, a touch panel, or the like. The display 23 displays a GUI used by the operator of the ultrasonic diagnostic apparatus 20 to input various instructions and setting requests via the input interface 22, an ultrasonic image generated by the apparatus main body 24, and an analysis result obtained when performing distance measurement or the like for the ultrasonic image. The display 23 can switch between display of the B-mode image and display of the Doppler image.

The apparatus main body 24 generates an ultrasonic image using the reflected waves received by the ultrasonic probe 21. As shown in FIG. 4, the apparatus main body 24 includes the transmission/reception circuitry 241, storage 242, and processing circuitry 244.

The transmission/reception circuitry 241 is electric circuitry including combining trigger generation circuitry, transmission delay circuitry, and pulser circuitry. The transmission/reception circuitry 241 supplies a driving signal to the ultrasonic probe 21. The pulser circuitry repeatedly generates rate pulses for forming ultrasonic waves at a predetermined repetition frequency (PRF). The transmission delay circuitry gives each rate pulse generated by the pulser circuitry a transmission delay time for each piezoelectric transducer necessary to focus an ultrasonic pulse generated by the ultrasonic probe 21 into a beam and determine transmission directivity. The trigger generation circuitry applies a driving signal (driving pulse) to the ultrasonic probe 21 at the timing depending on the rate pulse. That is, the transmission delay circuitry arbitrarily adjusts the transmission direction from the surface of each piezoelectric transducer by changing the transmission delay time given to each rate pulse.

The transmission/reception circuitry 241 includes amplification circuitry, an A/D (Analog/Digital) converter, reception delay circuitry, an adder, and quadrature detection circuitry. The transmission/reception circuitry 241 performs various processes for the reflected wave signal received by the ultrasonic probe 21, thereby generating reflected wave data. The amplification circuitry amplifies the reflected wave signal for each channel, and performs gain correction processing. The A/D converter A/D-converts the reflected wave signals having undergone gain correction. The reception delay circuitry gives digital data reception delay times necessary to determine reception directivities. The adder performs the addition processing of the reflected wave signals which have been given the reception delay times by the reception delay circuitry. The addition processing by the adder enhances reflected components in directions according to the reception directivities of the reflected wave signals.

The storage 242 stores an ultrasonic image generated by an image processing function 244d of the processing circuitry 244 (to be described later), an image generated by performing image processing for the ultrasonic image by an image processing function 244d, apparatus control programs for performing ultrasonic transmission/reception, image processing, and display processing, and various data such as diagnosis information (for example, a patient ID) and various kinds of setting information. The storage 242 may include, for example, a semiconductor memory element such as a RAM (Random Access Memory) and a flash memory, a hard disk, and an optical disk.

The processing circuitry 244 includes a system control function 244a, a B-mode processing function 244b, a Doppler processing function 244c, the image processing function 244d, and a communication control function 244e.

The system control function 244a controls the overall processing in the ultrasonic diagnostic apparatus 20. More specifically, the system control function 244a controls the processes of the transmission/reception circuitry 241, B-mode processing function 244b, Doppler processing function 244c, and image processing function 244d and controls to display the ultrasonic image stored in the storage 242 and the like on the display 23, using the various instructions and setting requests input from the operator via the input interface 22, the various programs loaded from the storage 242, and the various kinds of setting information.

The B-mode processing function 244b generates data (B-mode data) in which the signal intensity is expressed by the brightness of luminance by receiving the reflected wave data from the transmission/reception circuitry 241 and performing logarithmic amplification, envelope detection processing, and the like.

The Doppler processing function 244c generates data (Doppler data) by performing frequency analysis for velocity information from the reflected wave data received from the transmission/reception circuitry 241, extracting blood, tissue, and a contrast medium echo component by the Doppler effect, and extracting moving body information such as mean velocities, variances, and powers at multiple points.

The image processing function 244d generates an ultrasonic image from the B-mode data generated by the B-mode processing function 244b, and generates an ultrasonic image from the Doppler data generated by the Doppler processing function 244c. More specifically, the image processing function 244d generates a B-mode image from the B-mode data and generates a Doppler image from the Doppler data. In addition, the image processing function 244d performs coordinate conversion and data interpolation to convert (scan a barcode) a scanning line signal sequence by an ultrasonic scan into a scanning line signal sequence in a video format represented by a TV format, thereby generating ultrasonic images (B-mode image, Doppler image) as display images.

The communication control function 244e controls communication performed with another apparatus via the network 50. For example, the communication control function 244e transfers, via the network 50, the ultrasonic image generated by the image processing function 244d to the other apparatus. The ultrasonic image transferred via the network 50 can undergo image display, image processing, or the like in the transfer destination apparatus. The communication control function 244e receives image data transferred from the other apparatus via the network 50.

Furthermore, each of the processing functions performed by the system control function 244a, B-mode processing function 244b, Doppler processing function 244c, image processing function 244d, and communication control function 244e as the components of the processing circuitry 244 is recorded in the storage 242 in a form of a medical information processing program executable by a computer. The processing circuitry 244 is a processor for implementing a function corresponding to each medical information processing program by reading out the medical information processing program from the storage and executing it. In other words, the processing circuitry 244 which has read out each medical information processing program has each function shown in the processing circuitry 244 of FIG. 4. Note that in FIG. 4, each of the processing functions implemented by the system control function 244a, B-mode processing function 244b, Doppler processing function 244c, image processing function 244d, and communication control function 244e is implemented by the single processing circuitry 244. The present invention, however, is not limited to this. A plurality of independent processors may be combined to form the processing circuitry 244, and each processor may execute the medical information processing program to implement each processing function.

[Image Output Apparatus]

The image output apparatus 40 acquires a mammography image and an overlay image including a finding comment about the mammography image from the medical image processing apparatus 30, and displays them. Note that the display 23 of the ultrasonic diagnostic apparatus 20 may be used as the image output apparatus 40. In this case, the image output apparatus 40 including the display 23 may display an ultrasonic image in addition to the mammography image and the overlay image. The image output apparatus 40 is mainly used by the operator of ultrasonic examination to perform ultrasonic examination. For example, the image output apparatus 40 is a tablet terminal which is portable by the operator and is connectable to the network 50 via a wireless LAN (Local Area Network). Note that the image output apparatus 40 may be, for example, a notebook PC or a printing apparatus such as a printer.

[Medical Image Processing Apparatus]

Referring back to FIG. 1, the medical image processing apparatus 30 is configured to be connected to the mammography apparatus 10, and has a function of performing processing of interpreting the mammography images generated by the mammography apparatus 10. The medical image processing apparatus 30 accepts an input of a finding comment about the mammography images from the operator of mammography examination, and stores information indicating the accepted finding comment. For example, the medical image processing apparatus 30 may be realized by a workstation.

Figure 5:
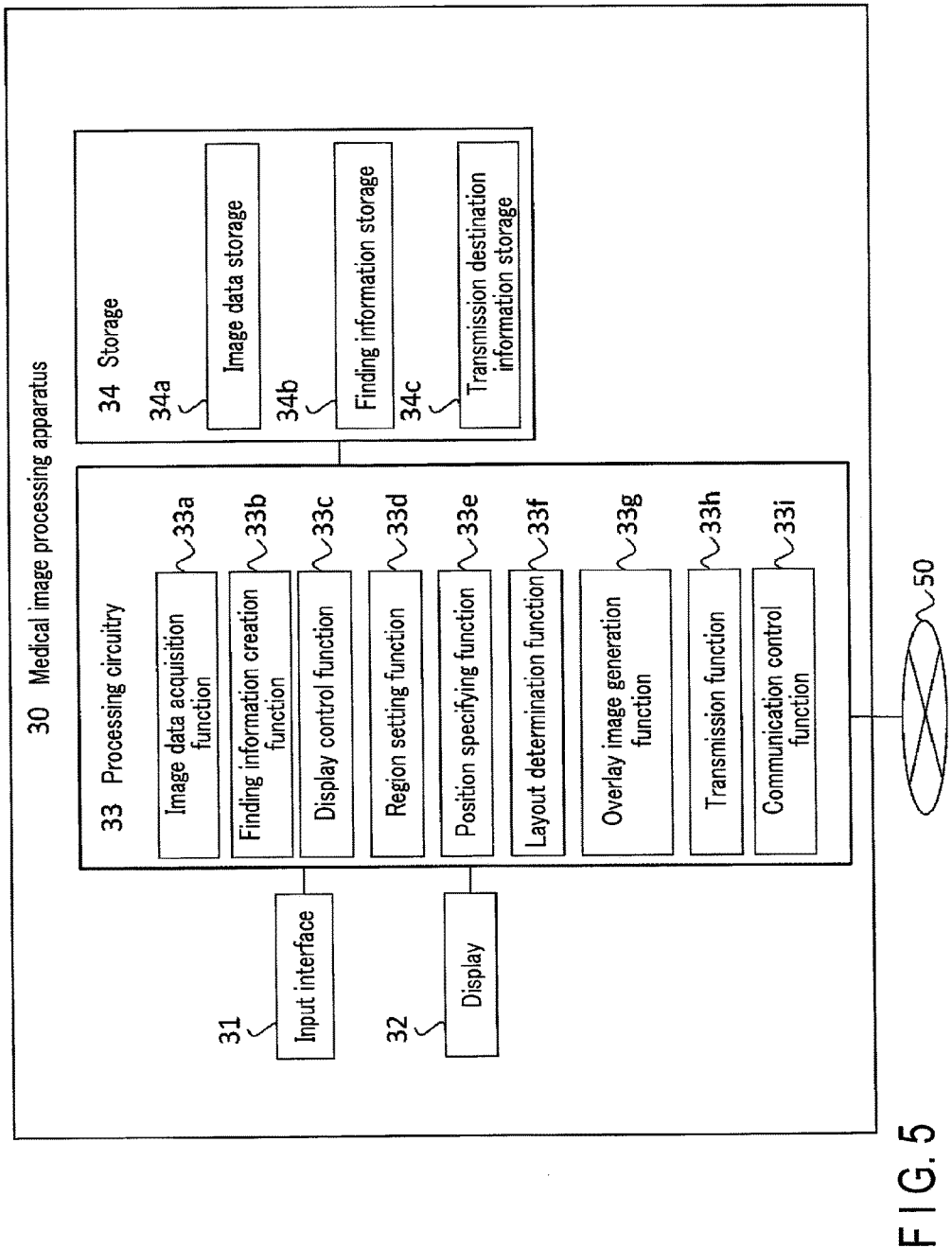
FIG. 5 is a block diagram showing an example of the arrangement of a medical image processing apparatus according to the embodiment.

FIG. 5 is a block diagram showing an example of the arrangement of the medical image processing apparatus 30 according to the embodiment. As shown in FIG. 5, the medical image processing apparatus 30 includes an input interface 31, a display 32, processing circuitry 33, and a storage 34.

The input interface 31 accepts various operations from the operator, and input of various kinds of information. For example, the input interface 31 may include a keyboard, a mouse, buttons, a trackball, a touch panel, and the like. Note that the input interface 31 is not limited to circuitry including physical operation parts such as a mouse and keyboard. For example, examples of the input interface 31 include circuitry for receiving an electrical signal corresponding to an instruction input from an external input device provided separately from the medical image processing apparatus 30, and outputting the electrical signal to the processing circuitry 33.

The display 32 may include a liquid crystal display, a CRT display, a touch panel, or the like. The display 32 displays a GUI for accepting various operations from the operator, and various images.

The processing circuitry 33 includes an image data acquisition function 33a, a finding information creation function 33b, a display control function 33c, a region setting function 33d, a position specifying function 33e, a layout determination function 33f, an overlay image generation function 33g, a transmission function 33h, and a communication control function 33i.

The storage 34 is a storage device including a hard disk and a semiconductor memory, and stores various kinds of information. The storage 34 includes image data storage 34a, finding information storage 34b, and transmission destination information storage 34c.

The image data storage 34a stores mammography images obtained by capturing a breast of an object, and the imaging directions of the mammography images. More specifically, the image data storage 34a stores, for each image, a mammography image and information indicating an imaging direction in association with each other. The information indicating the imaging direction of the mammography image is, for example, information representing whether the imaging direction of the breast of the object is an MLO (Mediolateral-Oblique) direction or CC (Cranio-Caudal) direction.

The image data acquisition function 33a (to be described later) stores mammography images and pieces of information respectively indicating imaging directions in the image data storage 34a. In addition, the image data storage 34a stores DICOM (Digital Imaging and Communication in Medicine) data generated by the overlay image generation function 33g (to be described later). The above-described DICOM data are medical image data complying with the DICOM standard, and each includes image data and additional information such as patient information. The additional information of the DICOM data according to this embodiment includes the imaging direction of the mammography image. The mammography images stored in the image data storage 34a correspond to a mammography image (MLO image) in the MLO direction and a mammography image (CC image) in the CC direction.

The finding information storage 34b stores interpretation information such as a finding comment about mammography images of an object. The finding information creation function 33b of the processing circuitry 33 (to be described later) records the finding comment in the finding information storage 34b.

The transmission destination information storage 34c stores information about at least one of the display 32, the display 23 of the ultrasonic diagnostic apparatus 20, and the image output apparatus 40, on which a mammography image and an overlay image (second image) obtained by arranging a schematic diagram of the breast corresponding to the mammography image, a region of interest ROI, a finding comment, and the like is displayed. FIG. 6 is a table showing an example of the information stored in the transmission destination information storage 34c. Examples of the information stored in the transmission destination information storage 34c include information about the types of the display 32, the display 23 of the ultrasonic diagnostic apparatus 20, and the image output apparatus 40 as transmission destinations, the screen sizes of the display 32, the display 23 of the ultrasonic diagnostic apparatus 20, and the image output apparatus 40, transmission methods to the display 32, the display 23 of the ultrasonic diagnostic apparatus 20, and the image output apparatus 40, and transmission rates to the display 32, the display 23 of the ultrasonic diagnostic apparatus 20, and the image output apparatus 40. These pieces of information are stored in correspondence with each of the display 32, the display 23 of the ultrasonic diagnostic apparatus 20, and the image output apparatus 40.

The image data storage 34a, finding information storage 34b, and transmission destination information storage 34c as the components of the storage 34 may be separately provided as circuitry, or may be configured to store the respective pieces of information by dividing the memory area of storage.

The storage 34 may be provided, as an image saving server, separately from the medical image processing apparatus 30.

The image data acquisition function 33a acquires mammography images obtained by capturing the breasts of the object, and pieces of information respectively indicating the imaging directions of the mammography images. Note that the image data acquisition function 33a acquires an MLO image and a CC image for each of the right and left breasts of the object. More specifically, the image data acquisition function 33a acquires mammography images about the object to be diagnosed and pieces of information respectively indicating the imaging directions of the mammography images by communicating with the mammography apparatus 10 via the communication control function 33i (to be described later). The image data acquisition function 33a stores the acquired mammography images and the acquired pieces of information respectively indicating the imaging directions in the image data storage of the storage 34 (to be described later).

The finding information creation function 33b accepts a finding comment about the mammography images of the object input from the operator. The finding information creation function 33b stores the accepted finding comment in the finding information storage 34b of the storage 34 in association with the mammography images.

The display control function 33c displays, on the display 32, a reference image for referring to the mammography images. More specifically, when accepting a mammography image display request from the operator via the input interface 31, the display control function 33c reads out, from the image data storage 34a, mammography images related to the object to be diagnosed, and reads out, from the finding information storage 34b, a finding comment about the object to be diagnosed. The display control function 33c displays, on the display 32, a reference image in which the readout mammography images and finding comment are arranged.

The region setting function 33d sets a region of interest in each mammography image. For example, the region setting function 33d sets a region of interest in each of the MLO image and CC image for each of the right and left breasts of the object. More specifically, the region setting function 33d accepts, via the input interface 31, from the operator, an operation of designating a range of an arbitrary size at an arbitrary position on each of the mammography images arranged in the reference image displayed by the display control function 33c. The region setting function 33d then sets, as a region of interest, the range designated by the operator. The position of the designated region of interest is displayed on the mammography image by a marker such as a graphic. Furthermore, if there are a plurality of regions of interest, the region setting function 33d may set regions of interest by changing the shapes of markers or changing the colors of displayed markers so that the operator can discriminate between them. Instead of the region of interest, a point (coordinate point) on the mammography image may be pointed.

Note that, for example, the region setting function 33d may automatically detect a candidate region of a lesion portion from each mammography image using a computer aided diagnosis (CAD) function, and set the detected region as a region of interest. For example, the region setting function 33d may accept an operation in which the operator adjusts regions detected by the CAD between the MLO image and the CC image, and then set the adjusted regions as regions of interest.

Using the position information of the region of interest on each mammography image and the information indicating the imaging direction, the position specifying function 33e specifies the position information of the region of interest on the schematic diagram schematically representing the breast. The position information of the region of interest on the schematic diagram represents information indicating the coordinate position of the region of interest on the schematic diagram and the size (for example, the diameter) of the region of interest. More specifically, the position specifying function 33e reads out, from the image data storage 34a, a mammography image of the object to be examined, and information indicating the imaging direction of the mammography image. Then, the position specifying function 33e specifies the position of the region of interest on the schematic diagram using the readout mammography image and the readout information indicating the imaging direction. Note that various diagrams such as a diagram indicating the positional relationship in the breast can be used as the schematic diagram (also called a scheme).

In response to an instruction from the operator, the transmission function 33h transmits the mammography images and the overlay images generated by the overlay image generation function 33g to the ultrasonic diagnostic apparatus 20 or the image output apparatus 40. The transmission function 33h accepts a transmission request of the overlay images and mammography images, which has been input via the input interface 31. The transmission function 33h accepts, via the network 50, the transmission request of the overlay images and mammography images, which has been input via the input interface 22 by the operator of the ultrasonic diagnostic apparatus 20. Upon accepting the transmission request of the overlay images and mammography images, the transmission function 33h reads out, from the storage 34, the overlay images and mammography images, which have been designated by the operator. The transmission function 33h transmits the readout overlay images and mammography images to the ultrasonic diagnostic apparatus 20 or the image output apparatus 40.

The communication control function 33i controls communication performed with another apparatus via the network 50. For example, the communication control function 33i is connected to the network 50 via the wireless LAN to perform wireless communication with the other apparatus. Note that communication between the medical image processing apparatus 30 and the other apparatus, which has been performed by the communication control function 33i via the network 50 is not limited to the above-described one as long as electrical signals are exchanged. For example, the medical image processing apparatus 30 may be configured to communicate with the image output apparatus 40 such as a printer in accordance with the communication standard such as USB.

Furthermore, each of the processing functions performed by the image data acquisition function 33a, finding information creation function 33b, display control function 33c, region setting function 33d, position specifying function 33e, layout determination function 33f, overlay image generation function 33g, transmission function 33h, and communication control function 33i as the components of the processing circuitry 33 is recorded in the storage 34 in a form of a medical information processing program executable by a computer. The processing circuitry 33 is a processor for implementing a function corresponding to each medical information processing program by reading out the medical information processing program from the storage and executing it. In other words, the processing circuitry 33 which has read out each medical information processing program has each function shown in the processing circuitry 33 of FIG. 5. Note that in FIG. 5, each of the processing functions of the image data acquisition function 33a, finding information creation function 33b, display control function 33c, region setting function 33d, position specifying function 33e, layout determination function 33f, overlay image generation function 33g, transmission function 33h, and communication control function 33i is implemented by the single processing circuitry 33. The present invention, however, is not limited to this. A plurality of independent processors may be combined to form the processing circuitry 33, and each processor may execute the medical information processing program to implement each processing function.

Figure 7A:
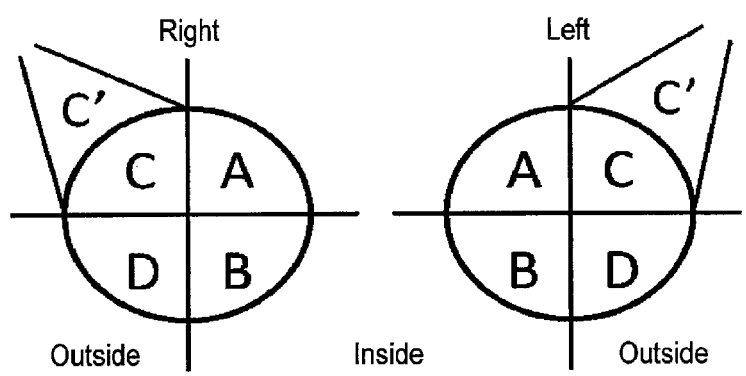
FIG. 7A is a view showing an example of a schematic diagram according to the embodiment.
Figure 7B:
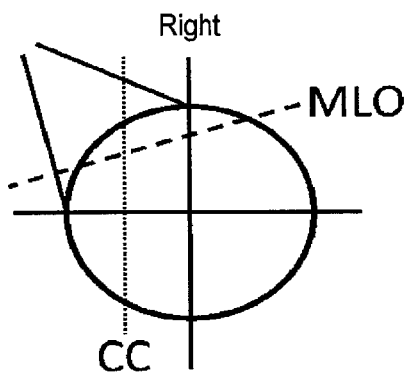
FIG. 7B is a view showing another example of the schematic diagram according to the embodiment.

FIGS. 7A and 7B are views each showing an example of the schematic diagram used by the position specifying function 33e according to the embodiment. In the example shown in each of FIGS. 7A and 7B, a schematic diagram of a mammary gland region is shown as an example of the schematic diagram schematically representing the breast. For example, as shown in FIG. 7A, the schematic diagram of the mammary gland region includes, for each of the right and left breasts, a circular region (to be referred to as a breast region hereinafter) representing a region of a breast and an almost triangular region (to be referred to as an armpit region hereinafter) representing a region of an armpit portion.

The circular region representing the breast region is divided vertically and horizontally into four regions "A" to "D". For example, the region "A" (to be referred to as region A hereinafter) indicates a region of the inside upper portion of the breast, and the region "B" (to be referred to as region B hereinafter) indicates a region of the inside lower portion of the breast. Furthermore, for example, the region "C" (to be referred to as region C hereinafter) indicates a region of the outside upper portion of the breast, and the region "D" (to be referred to as region D hereinafter) indicates a region of the outside lower portion of the breast. In addition, the almost triangular region "C'" (to be referred to as region C' hereinafter) representing the armpit region has a shape extending obliquely upward from region C and tapered as the distance from region C increases. Note that various diagrams can be used as the schematic diagram as long as they indicate the positional relationship in the breast. For example, a schematic diagram which three-dimensionally indicates the shape of the breast may be used.

FIG. 7B is a view obtained by adding, to the schematic diagram of the breast, the imaging directions of the mammography images when an abnormal finding is found in the right breast. Referring to FIG. 7B, lines indicating the imaging directions of the MLO image and CC image in each of which an abnormal finding is found are added. Based on the directions and positions of the straight lines drawn on the schematic diagram, which respectively correspond to the respective mammography images in each of which the abnormal finding is found, the operator of the ultrasonic diagnostic apparatus 20 can grasp the imaging directions of the mammography images in each of which the abnormal finding is found. If, for example, an abnormal finding is found in only one of the MLO image and the CC image, only the straight line indicating the imaging direction of the image in which the abnormal finding is found may be displayed.

Referring back to FIG. 5, the layout determination function 33f loads the pieces of information from the finding information storage 34b and the transmission destination information storage 34c to determine a layout on the display 32. At this time, the layout on the display 32 corresponds to, for example, the sizes of the mammography image, the schematic diagram of the breast, the graphic representing the region of interest, and the finding comment, and the arrangement relationship between them. The layout determination function 33f will be described in detail with reference to FIGS. 8A and 8B. When a "display" is simply described, it includes the display 23 of the ultrasonic diagnostic apparatus 20 and the image output apparatus 40.

FIGS. 8A and 8B are explanatory views for explaining details of the layout determination function 33f. The layout determination function 33f accepts a transmission request to transmit the mammography images and overlay images to the display 23 of the ultrasonic diagnostic apparatus 20 or the image output apparatus 40. Practical examples of the transmission request are acceptance of input information from the operator of the mammography apparatus 10 via the input interface 17a, and acceptance of input information from the operator of the ultrasonic diagnostic apparatus 20 via the input interface 22.

Next, the layout determination function 33f loads, from the transmission destination information storage 34c, the information about the transmission destination display shown in FIG. 8A and information about a transmission method, a transmission rate, and the like. The layout determination function 33f acquires a mammography image interpretation result shown in FIG. 8B from the finding information storage 34b. Information included in the acquired mammography image interpretation result includes, for example, image IDs, an interpretation ID, the coordinates and sizes of regions of interest, and a finding comment. The image IDs are assigned to the respective mammography images. For example, different image IDs are assigned to an MLO image and a CC image, both of which have been captured by one examination operation. The interpretation ID is the same number assigned to the MLO image and CC image, both of which have been captured by one examination operation. A different interpretation ID is assigned every time an examination operation is performed. Upon acquiring the information about the transmission destination display and the mammography image interpretation information, the layout determination function 33f determines the layout of each overlay image. In this example, the presence/absence of a region of interest is determined. If there is a region of interest, the layout of the display screen of the transmission destination is determined.

Figure 9:
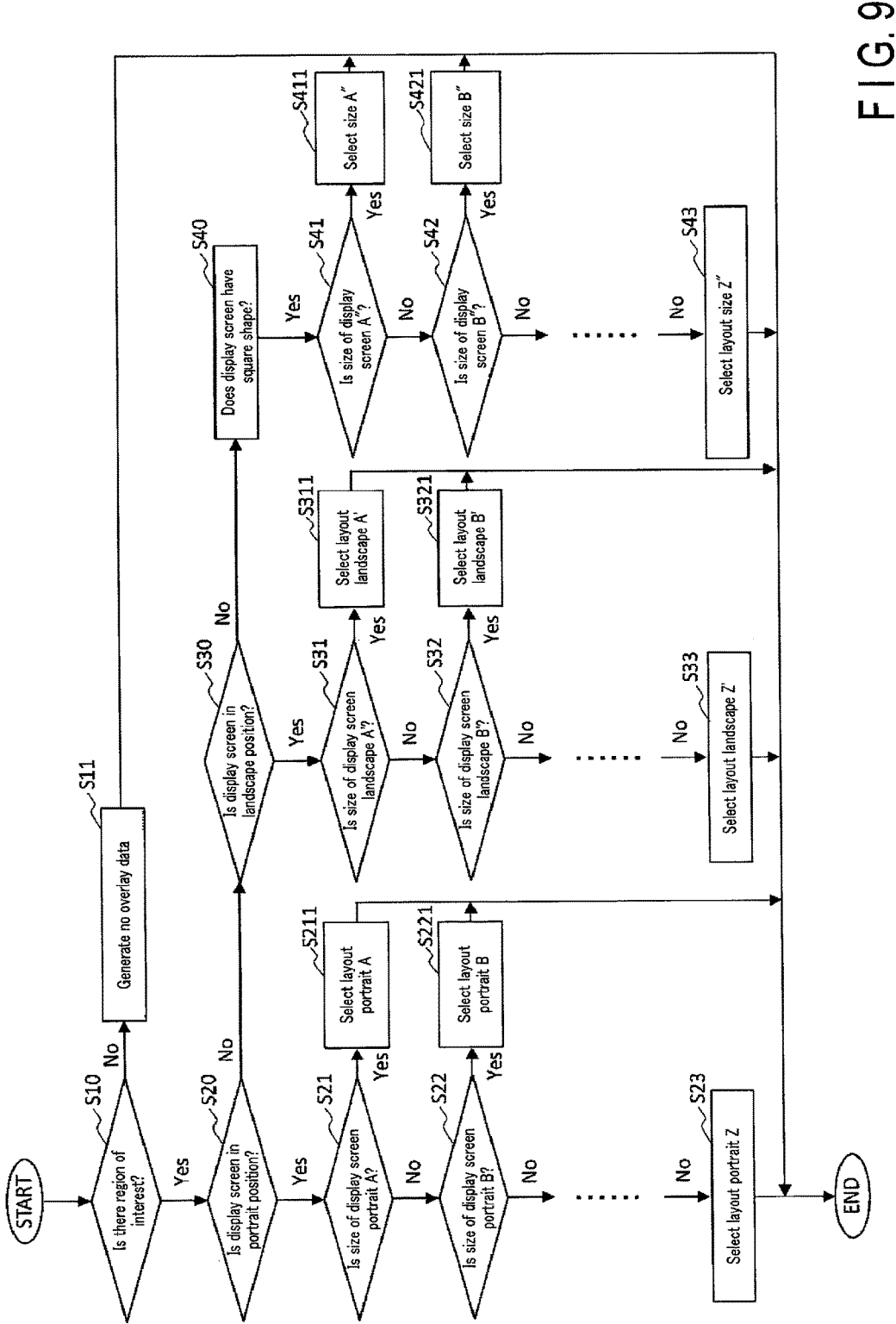
FIG. 9 is a flowchart illustrating a layout determination procedure according to the embodiment.

FIG. 9 is a flowchart illustrating an example of a method of determining the layout of each overlay image by the layout determination function 33f. First, the layout determination function 33f loads, from the image data storage 34a, a mammography image to be interpreted, and determines the presence/absence of a region of interest on the mammography image (step S10). If there is no region of interest (NO in step S10), the layout determination function 33f determines that it is unnecessary to generate an overlay image for the mammography image (step S11). If there is a region of interest (YES in step S10), the aspect ratio of the display screen, a screen size, a resolution, and the like are sequentially determined by the layout determination function 33f in subsequent steps after step S10.

In step S20, the layout determination function 33f determines whether the display screen of the display 23 of the ultrasonic diagnostic apparatus 20 and the display screen of the image output apparatus 40 (to be referred to as a display screen in this flowchart hereinafter) are in a portrait position. If the layout determination function 33f determines that the display screen is in the portrait position (YES in step S20), the size of the display screen in the portrait position is determined in step S21 and subsequent steps.

The layout determination function 33f loads information about the size of the display screen from the transmission destination information storage 34c. For example, the layout determination function 33f determines in steps S21 and S22 whether the display screen is "portrait A" or "portrait B". Note that "portrait A" and "portrait B" are examples of a classification item for classifying the size and shape of the display screen. Each of "portrait A" and "portrait B" is linked with the layout of the display screen of a predetermined display in the transmission destination information storage 34c. If the layout determination function 33f detects a layout matching the display screen of the transmission destination (steps S211 or S221), determination of the layout ends. If determination is performed for the number of display screens, which is equal to a number obtained by subtracting one from the number of display screens loaded by the layout determination function 33f from the transmission destination information storage 34c, and no desired display screen is detected, the layout (portrait Z) of the remaining display screen is determined (step S23), the layout determination processing ends.

If the layout determination function 33f determines in step S20 that the display screen is not in the portrait position, it is determined in step S30 whether the display screen is in a landscape position. If it is determined that the display screen is in the landscape position (YES in step S30), processes similar to those performed in steps S21 to S23 are executed in steps S31 to S33 to determine the size of the display screen. If it is determined that the display screen is not in the landscape position (NO in step S30), the display screen is determined to have a square shape (step S40). After that, processes similar to those performed in steps S21 to S23 are executed in steps S41 to S43 to determine the size of the display screen.

The above-described flowchart has been explained by assuming that if there is no region of interest, no overlay image is generated. The present invention, however, is not limited to this. Even if there is no region of interest, an overlay image may be generated exceptionally. In this case, the overlay image generation function 33g generates only an overlay image on which a comment indicating that there is no abnormal finding is displayed.

Figure 10:
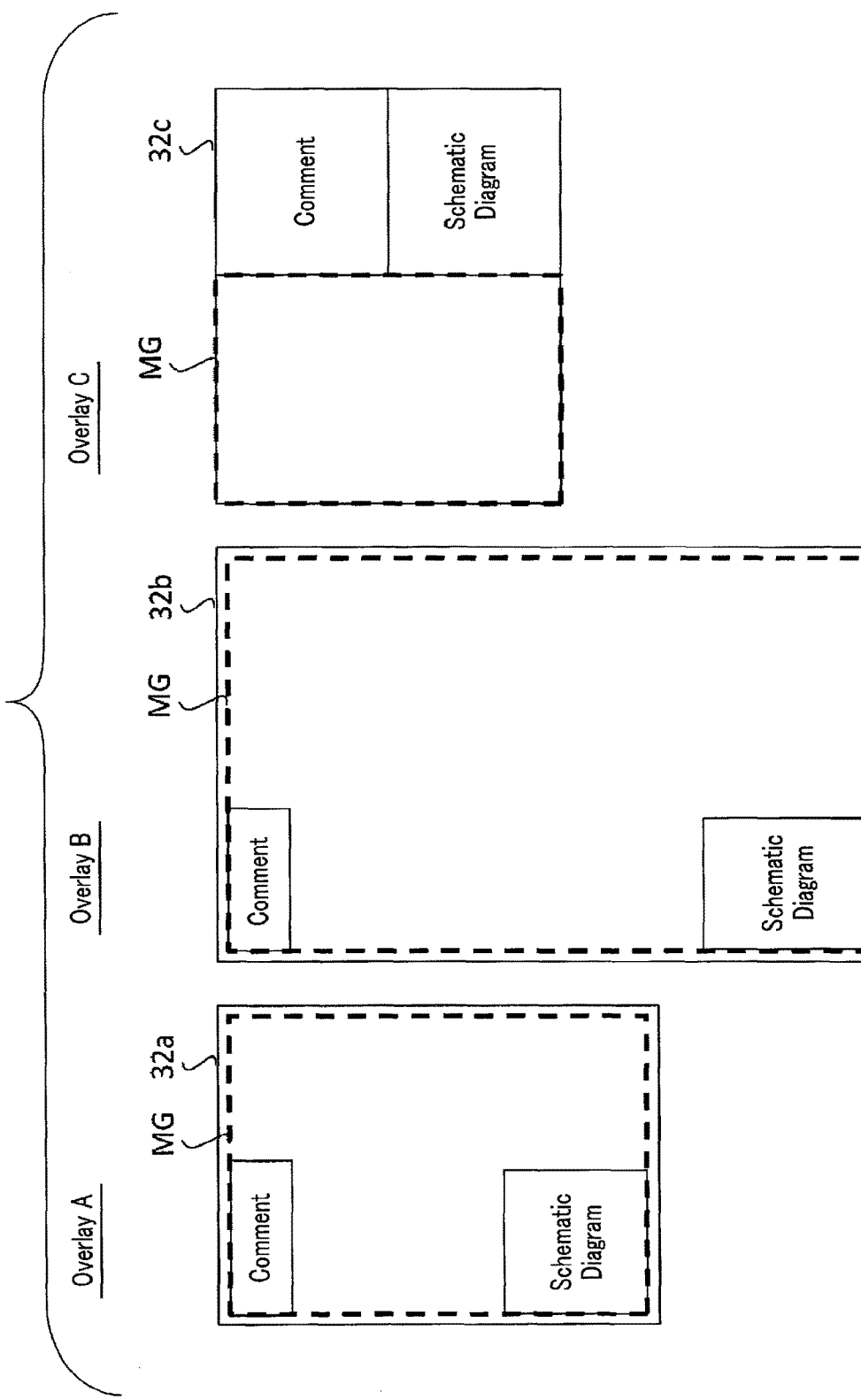
FIG. 10 is a view for explaining examples of the layout of an overlay image according to the embodiment.

FIG. 10 is a view showing examples of the layout of an overlay according to the screen size of the transmission destination display. In overlay A, a mammography image is displayed in a range surrounded by dotted lines within a display screen 32a of the display. Thus, a comment and a schematic diagram are arranged at corners of the display screen not to be superimposed on a region of the breast in a mammography image MG. The display screen 32a in overlay A is smaller than a display screen 32b in overlay B. However, it is not desirable to excessively increase or decrease the sizes of the comment and schematic diagram depending on the size of the display screen. Therefore, it is desirable to adjust the apparent sizes of the comment and schematic diagram to the sizes which the operator of the ultrasonic diagnostic apparatus readily visually perceives, and arrange the comment and schematic diagram, even if the size of the display screen is changed. For example, the size of the schematic diagram or the like arranged in overlay A is desirably set to be equal to that in overlay B. If the display screen is in the portrait position, the portrait mammography image may be arranged and displayed by enlarging a region of the mammography image where the breast is displayed without displaying a region including no breast. At this time, the schematic diagram or the like is desirably arranged at the lower or upper left of the mammography image not to overlap the breast region (first layout). If the display screen is in the landscape position, a region other than the breast region of the mammography image may also be displayed, and the schematic diagram or the like may be arranged in the region other than the breast region (second layout). As indicated by a display screen 32c in overlay C, if the screen size of the display is relatively small, a region for displaying the finding comment and schematic diagram may be provided beside the display region of the mammography image MG, thereby arranging the finding comment and schematic diagram not to overlap the display region of the mammography image MG. Furthermore, since the finding comment and schematic diagram may overlap the breast in the mammography image MG, the finding comment and schematic diagram may be displayed to be discriminated from the mammography image MG by, for example, filling the backgrounds, frames, and the like of the finding comment, the schematic diagram, and the like with another color to be discriminated from the background of the mammography image MG. The above-described processing of filling the backgrounds, frames, and the like of the finding comment, the schematic diagram, and the like with another color to be discriminated from the background of the mammography image MG includes execution of display to enable discrimination by changing the grayscale levels.

The presence/absence of display of the overlay image may be switched by accepting input information from the operator via the input interface 31. If there is no abnormal finding, only a comment indicating that there is no abnormal finding may be overlaid. If the display 32 can ensure a screen size to some extent, the CC image and MLO image may be arranged as one image. If a data communication band is narrow like in an examination car and/or if there is no abnormal finding, the mammography image may be compressed to decrease the data capacity, and then transmitted to the display 32. For example, in a communication environment such as an examination car in which the transmission rate is relatively low, the display size of the mammography image may be decreased to reduce its data capacity, and then the mammography image may be transmitted. Furthermore, if the image output apparatus 40 is formed by a printing apparatus such as a printer, the size of each printing sheet and the layout of a portrait or landscape overlay image according to each size may be stored in advance in the image data storage 34a.

The overlay image generation function 33g has a function of loading the layout of an overlay as the layout determined by the layout determination function 33f, and generating an overlay image.

Figure 11A:
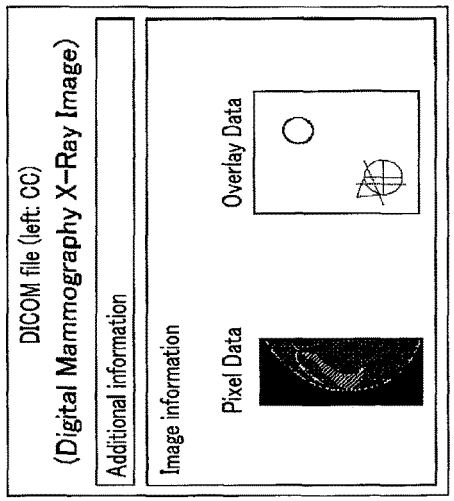
FIG. 11A is the first explanatory view for explaining a layout generation function according to the embodiment.
Figure 11B:
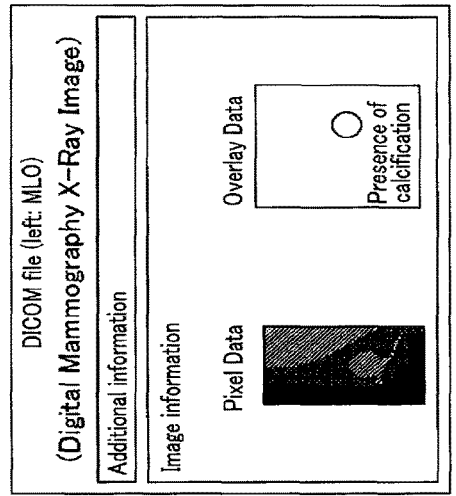
FIG. 11B is the second explanatory view for explaining the layout generation function according to the embodiment.

FIGS. 11A, 11B, 11C, and 11D are explanatory views for explaining details of the overlay image generation function 33g. The overlay image generation function 33g acquires mammography image interpretation information shown in FIG. 11A from the finding information storage 34b. The above-described interpretation information includes the position coordinates of the regions of interest on the mammography images, the sizes of the regions of interest, data indicating the acquisition positions of the MLO image and CC image, and a finding comment. Next, the overlay image generation function 33g receives the layout of the overlay from the layout determination function 33f, and generates overlay images. For example, as shown in FIG. 11B, circles corresponding to the coordinates and sizes of the regions of interest in the CC image and MLO image are set as the regions of interest based on the interpretation information shown in FIG. 11A. The position of the schematic diagram, the position of graphics indicating the regions of interest, and the position and size of finding comment are predetermined based on the layout of the overlay. Thus, overlay images in which the schematic diagram, the graphics indicating the regions of interest, and the finding comment are adjusted to the predetermined positions are generated. An image ID corresponding to each mammography image is assigned to each overlay image. For example, if overlay images in the MLO and CC directions are generated, the image IDs are respectively assigned to the overlay images. The overlay images are linked with the same interpretation ID.

Figure 11D:
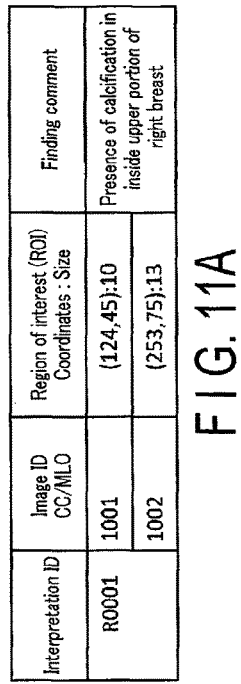
FIG. 11D is the fourth explanatory view for explaining the layout generation function according to the embodiment.
Figure 11C:
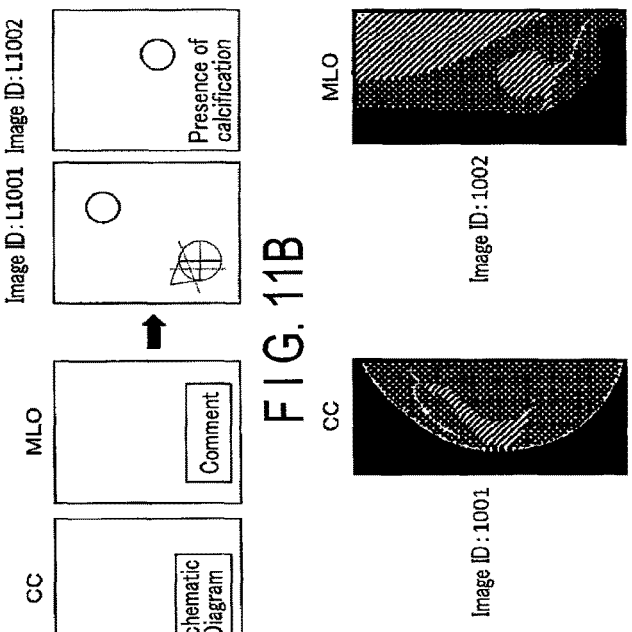
FIG. 11C is the third explanatory view for explaining the layout generation function according to the embodiment.

After the overlay images are generated, the overlay image generation function 33g acquires mammography images shown in FIG. 11C from the image data storage 34a. The overlay image generation function 33g generates DICOM files from the overlay images and the mammography images. The generated overlay images are stored in the DICOM files as pieces of image information of the DICOM files together with the mammography images, as shown in FIG. 11D. The generated DICOM files are temporarily stored in the image data storage 34a of the storage 34. The overlay images need not always be stored in the storage 34 as the pieces of image information of the DICOM files. The overlay images may be stored in the storage 34 as pieces of addition information. In the additional information, for example, the position coordinates of the region of interest, the shape and size of the type of marker for displaying the region of interest, information about the acquisition position of the mammography image in the schematic diagram, contents of the finding comment, and the like are saved. At this time, instead of being generated by the medical image processing apparatus 30, the overlay images may be generated on the side of the ultrasonic diagnostic apparatus 20 and/or the image output apparatus 40 when the ultrasonic diagnostic apparatus 20 and/or the image output apparatus 40 receives the above-described pieces of additional information.

The transmission function 33h (to be described later) transmits, to the ultrasonic diagnostic apparatus 20 or the image output apparatus 40 via the mammography apparatus 10, the DICOM files generated by the overlay image generation function 33g. Upon receiving the overlay images and the mammography images, the display 23 of the ultrasonic diagnostic apparatus 20 or the image output apparatus 40 superimposes and displays the overlay images on the mammography images. This makes it possible to display, on the display 23 or the image output apparatus 40, the schematic diagram, the regions of interest, and the finding comment in the layout according to the size and shape of the display 23 or the image output apparatus 40 using the desired layout of the mammography images. The graphic indicating the region of interest, the schematic diagram, the finding comment, and the like which are superimposed and displayed on the mammography image may be collectively referred to as an overlay image hereinafter.

[Operation]

Figure 12:
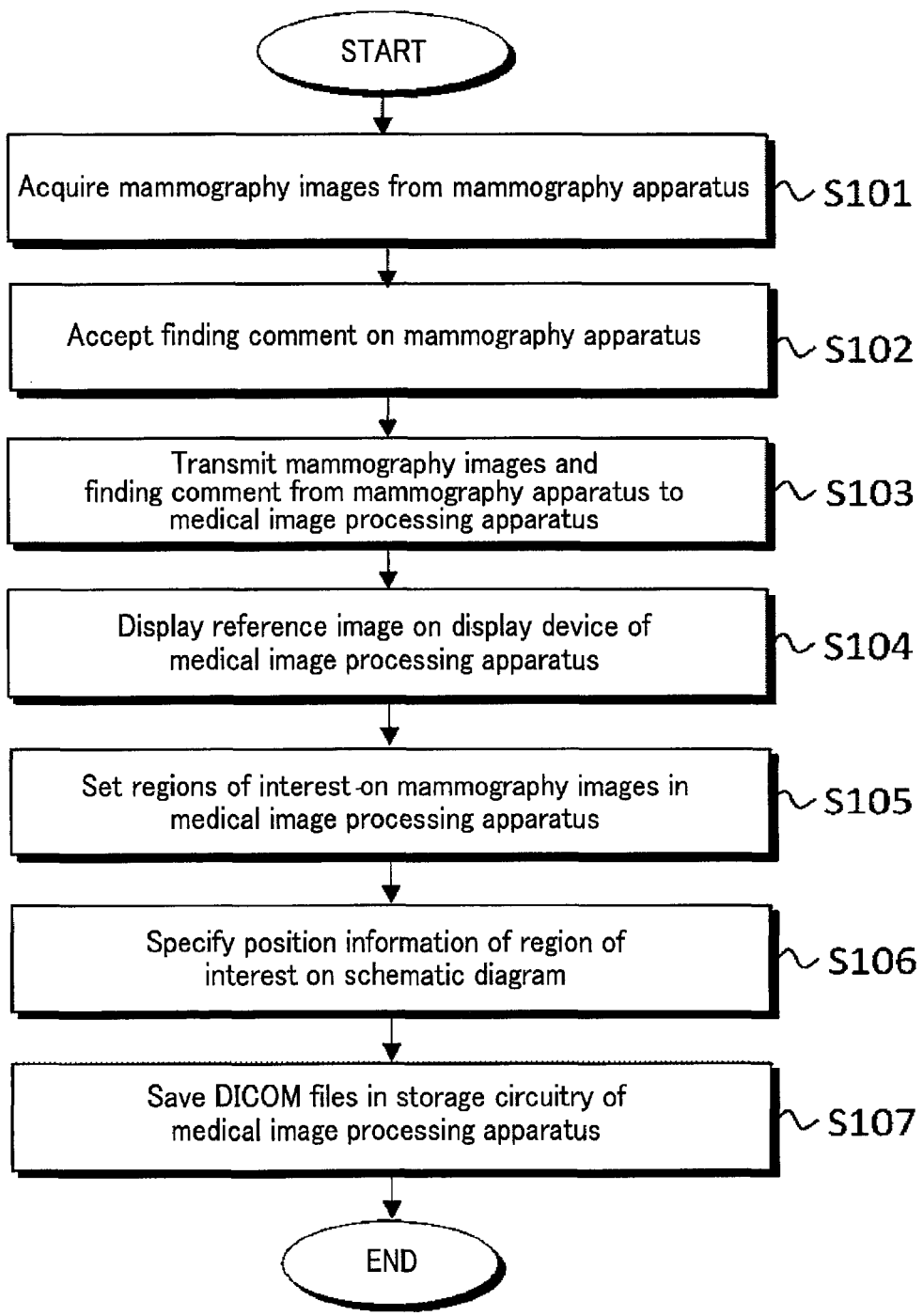
FIG. 12 is a flowchart for explaining an example of processing according to the embodiment.

FIGS. 12 and 13 are flowcharts each illustrating a processing procedure performed by the medical information processing system 100 according to this embodiment. FIG. 12 is a flowchart illustrating processing from obtaining of mammography images by the mammography apparatus 10 to generation of overlay images.

The mammography apparatus 10 accepts input information from the operator via the input interface 17a, performs X-ray imaging for each of the right and left breasts of the object, and captures mammography images in the MLO and CC directions. Each captured mammography image is temporarily stored in the storage 17d of the mammography apparatus 10. At this time, a corresponding image ID is assigned to each mammography image to generate a DICOM file.

The image data acquisition function 33a of the medical image processing apparatus 30 acquires desired mammography images from the storage 17d of the mammography apparatus 10 (step S101).

The finding information creation function 33b of the medical image processing apparatus 30 accepts input information from the operator of the mammography apparatus 10, and creates a finding comment about the breast of the object (step S102). The created finding comment is stored in the finding information storage 34b.

The mammography apparatus 10 transmits the mammography images and finding comment to the medical image processing apparatus 30 in a DICOM file format (step S103).

Subsequently, the display control function 33c of the medical image processing apparatus 30 displays, on the display 32, a reference image for referring to the mammography images (step S104).

After that, the region setting function 33d of the medical image processing apparatus 30 accepts, from the operator, via the input interface 31, an operation of designating desired ranges on the mammography images in the MLO and CC direction arranged on the reference image, and sets the designated ranges as regions of interest (step S105).

If the regions of interest are set in the mammography image in the MLO direction and the mammography image in the CC direction, the position specifying function 33e specifies the position information of a region of interest on a schematic diagram using the pieces of position information of the regions of interest set in the respective images and pieces of information respectively indicating the imaging directions of the images (step S106).

If the position specifying function 33e specifies the regions of interest on the mammography images, the pieces of position information indicating the regions of interest and the like are stored as pieces of additional information in the DICOM files, and the DICOM files are stored in the image data storage 34a (step S107).

FIG. 13 is a flowchart illustrating processing from acceptance of the transmission request of the overlay images and mammography images from the operator of the ultrasonic diagnostic apparatus 20 to display of the images on the display 23 of the ultrasonic diagnostic apparatus 20 or the image output apparatus 40.

Upon accepting a display instruction of the mammography images, the finding comment, and the like from the operator (YES in step S201), the medical image processing apparatus 30 determines, via the layout determination function 33f, the display screen of the ultrasonic diagnostic apparatus 20 or the image output apparatus 40 as the request destination of transmission contents (step S202). Examples of the display instruction in step S201 correspond to acceptance of input information of interpretation completion and/or an imaging result from the operator of the mammography apparatus 10 via the input interface 17a and acceptance of input information from the operator of the ultrasonic diagnostic apparatus 20 via the input interface 31.

Next, the overlay image generation function 33g generates overlay images based on the layout determined by the layout determination function 33f, the mammography images loaded from the image data storage 34a, and the finding result about the mammography images loaded from the finding information storage 34b (step S203). More specifically, the overlay image generation function 33g loads the layout corresponding to each display screen from the layout determination function 33f. The overlay image generation function 33g generates an overlay image by adding, to the loaded layout, the schematic diagram, the graphic indicating the region of interest, the finding comment, and the like. At this time, an image ID is assigned to the overlay image, and the overlay image is stored in the DICOM file of the corresponding mammography image and stored in the image data storage 34a while being transmitted to the ultrasonic diagnostic apparatus 20 or the image output apparatus 40 via the mammography apparatus 10.

Upon receiving the overlay images and mammography images from the medical image processing apparatus 30, the ultrasonic diagnostic apparatus 20 and the image output apparatus 40 display an image obtained by superimposing and displaying the overlay images on the mammography images (step S204).

If the mammography images are displayed on the display 23 of the ultrasonic diagnostic apparatus 20, the medical image processing apparatus 30 need only transmit the DICOM files. If the mammography images are displayed on the image output apparatus 40, the image output apparatus 40 does not support display of the DICOM files, and thus transmits the images in an image format such as JPEG instead of the DICOM files. At this time, the overlay images and mammography images need to be transmitted in an image format such as JPEG.

By executing the series of processes, it is possible to provide, in accordance with the size and shape of the display screen on the display side, the arrangement of a display screen which the operator readily visually perceives.

(Modification)

The embodiment has explained a case in which one overlay image is generated for one mammography image. In this modification, a case in which a plurality of mammography images are composited into one image and one overlay image is generated for the composite image will be described with reference to FIG. 14.

Figure 14:
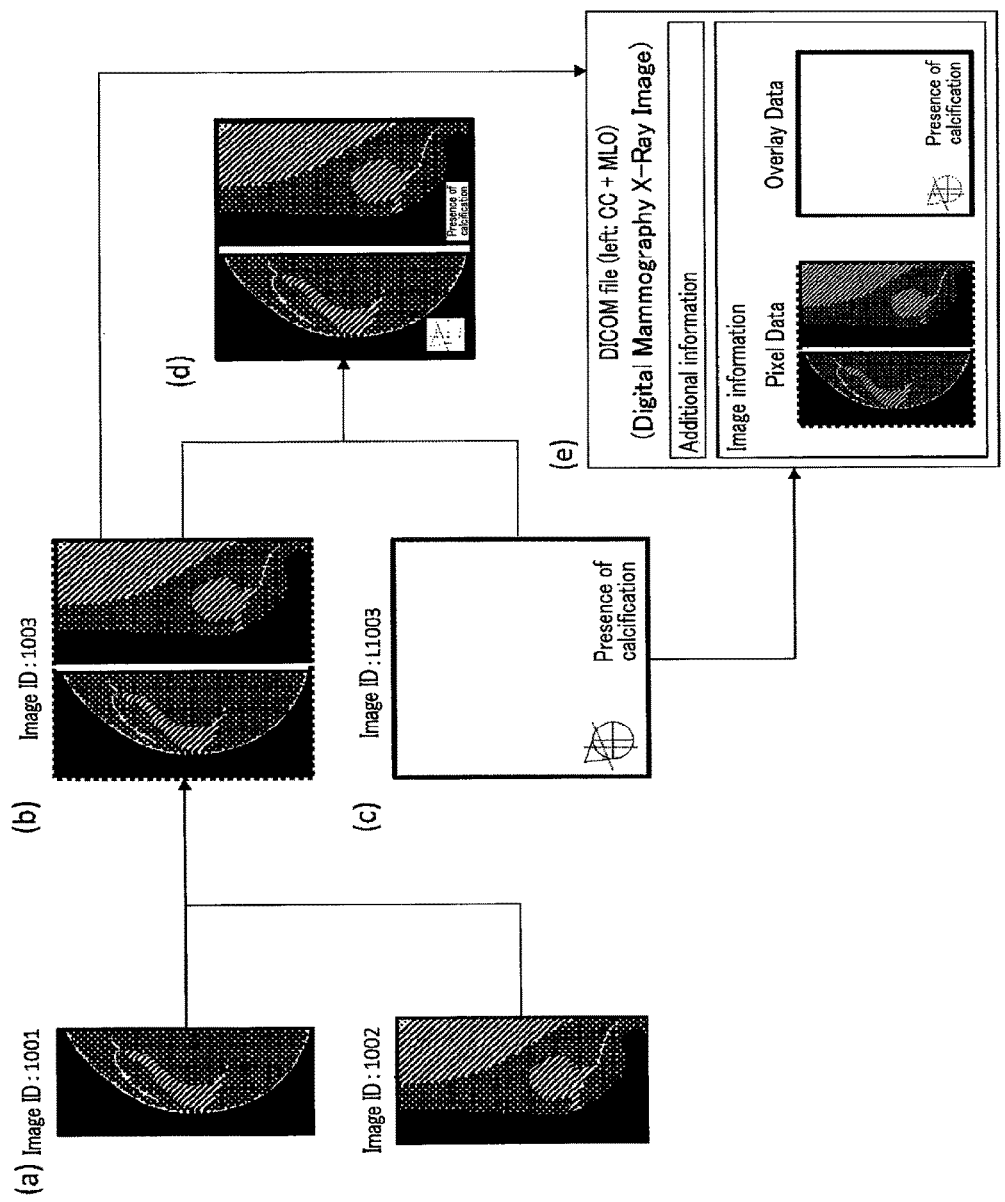
FIG. 14 is an explanatory view for explaining a modification of the embodiment.

FIG. 14 is a view for explaining an example of a method of generating a DICOM file in a secondary capture format. The DICOM file in the secondary capture format refers to an image file secondarily generated based on medical images generated by at least one modalities. For example, two medical images may be arranged and composed into one DICOM file in the secondary capture format. This modification will explain a case in which two medical images, that is, a CC image and an MLO image are composited to generate one composite image (to be referred to as an SC image (Secondary Capture image) hereinafter).

In the above description, the overlay image generation function 33g according to the embodiment receives the layout of the overlay from the layout determination function 33f, and generates an overlay image. The overlay image generation function 33g according to this modification further generates an SC image.

The overlay image generation function 33g acquires a plurality of mammography images from the image data storage 34a. In FIG. 14, (a) assumes that the acquired mammography images are a CC image and an MLO image. The overlay image generation function 33g generates an SC image by compositing the CC image and the MLO image into one image, as shown in (b) of FIG. 14. The SC image is sent from the overlay image generation function 33g to the layout determination function 33f. Upon accepting the SC image, the layout determination function 33f determines the layout of an overlay in accordance with the layout of the SC image, as shown in (c) of FIG. 14. The overlay image generation function 33g accepts the layout of the overlay from the layout determination function 33f, and generates an overlay image. An image is generated from the overlay image and SC image by superimposing and displaying the SC image, the schematic diagram, the graphics indicating the regions of interest, the finding comment, and the like, as shown in (d) of FIG. 14. The generated SC image and overlay image are converted into a DICOM file different from the DICOM files of the original mammography images, as shown in (e) of FIG. 14, and stored in the image data storage 34a. At this time, an image ID different from the original mammography images in the MLO and CC directions is assigned to the generated SC image, as shown in (b) of FIG. 14. In addition, an image ID is assigned to the overlay image. At this time, the interpretation ID of the SC image is desirably the same as the interpretation ID of the original mammography images.

The modification assumes that the SC image and the image obtained by superimposing and displaying the schematic diagram, the finding comment, and the like are converted into the DICOM file and saved in the image data storage 34a, and then transmitted to another medical image diagnostic apparatus such as the ultrasonic diagnostic apparatus 20 in the DICOM file format. However, the image saving format need not be the DICOM file format. For example, when displaying the images on the tablet terminal, an image file in the DICOM format cannot be displayed, and the image file of the mammography images and overlay image is saved in a format such as JPEG. Using the SC image described in the modification of the embodiment, the mammography images and overlay image may be used to generate an SC image, and the SC image may be saved in a format such as JPEG.

The above-described embodiment assumes that the transmission destination display is the display 23 of the ultrasonic diagnostic apparatus 20 or the image output apparatus 40 represented by the tablet terminal. However, these apparatuses may be used together as transmission destination displays. For example, if the ultrasonic diagnostic apparatus 20 and the tablet terminal are used together, only an ultrasonic image during ultrasonic image diagnosis may be displayed on the ultrasonic diagnostic apparatus 20, and the mammography images on which the overlay images are superimposed may be displayed on the tablet terminal. According to the above embodiment, it is possible to provide the operator with the arrangement of the easy-to-see mammography images, the schematic diagram, the graphics indicating the regions of interest, the finding comment, and the like in accordance with the screen sizes of the display screens of the transmission destinations. This can provide the schematic diagram and the like which the operator readily visually perceives even if, for example, the mammography images and overlay images are displayed on the tablet terminal or the like smaller than the display 23 of the ultrasonic diagnostic apparatus 20. This helps the operator of the ultrasonic diagnostic apparatus interpret the mammography images efficiently, and it can be expected to contribute to improvement of the examination efficiency and accuracy.

The above-described embodiment assumes that the overlay images are generated by the medical image processing apparatus 30 different from the mammography apparatus 10, the ultrasonic diagnostic apparatus 20, and the image output apparatus 40. An arrangement including no medical image processing apparatus 30 may be adopted. In this case, the mammography apparatus 10 may generate overlay images by having the function of the medical image processing apparatus 30.

If, contrary to the examination flow assumed by the embodiment, ultrasonic image diagnosis is performed, and then mammography examination is performed, an overlay image is generated for a precedingly acquired ultrasonic image, and displayed on the display 17e or the image output apparatus 40 at the time of capturing of mammography images.

When capturing diagnostic images of breasts, it can be assumed that ultrasonic examination and tomosynthesis examination are used together, instead of using the mammography examination and ultrasonic image diagnosis assumed in the embodiment. If ultrasonic examination and tomosynthesis examination are used together, an image obtained by superimposing and displaying a diagnostic image obtained by tomosynthesis examination and an overlay image may be displayed on the display of the ultrasonic diagnostic apparatus. Note that tomosynthesis examination is an examination method in which an X-ray image on an arbitrary slice of the object can be referred to by reconstructing a plurality of X-ray images captured from multiple directions. In tomosynthesis examination, the respective slices of the breast of the object can be displayed as a moving image. Thus, the overlay image generation function 33g of the medical image processing apparatus 30 may generate a layout by changing the arrangement and size of the schematic diagram in accordance with a slice to be displayed. If, for example, the breast of the object is captured in tomosynthesis examination, a slice on which the breast of the object is captured in a large size with respect to the size of the display screen of the display and a slice on which the breast is captured in a small size may be displayed. At this time, a layout for display of a moving image may be generated such that if a slice image of the breast is small with respect to the size of the display screen of the display, the schematic diagram and the like are displayed at positions not overlapping the breast on the slice image, and if the breast in a slice image is large, the schematic diagram and the like are not displayed. The sizes of the schematic diagram and the like may be changed in accordance with the display size of the breast in a slice image.

At the time of tomosynthesis examination, on the transmission destination display, all X-ray images acquired at the time of tomosynthesis examination may be displayed in a moving image format, or only a slice of a portion including an abnormal finding, among the X-ray images captured at the time of tomosynthesis examination, may be displayed as a still image. When displaying, on the display, as a moving image, the X-ray images acquired at the time of tomosynthesis examination, display may be performed so as to discriminate only a slice including an abnormal finding from other slices. For example, on only a slice including an abnormal finding, a marker or the like may be displayed in a portion where the abnormal finding is recognized.

The above-described embodiment assumes that upon accepting a display instruction of the mammography images, the finding comment, and the like from the operator, the medical image processing apparatus 30 determines, via the layout determination function 33f, the display screen of the ultrasonic diagnostic apparatus 20 or the image output apparatus 40 as the request destination of transmission contents. The embodiment is not limited to this. For example, when the medical image processing apparatus 30 accepts mammography images from the mammography apparatus 10, it may generate overlay images corresponding to all the display screens of a plurality of transmission destinations stored in advance in the transmission destination information storage 34c of the storage 34. With this processing, when the medical image processing apparatus 30 accepts a transmission request from each of the external mammography apparatus 10, ultrasonic diagnostic apparatus 20, and image output apparatus 40, it can transmit only the overlay images corresponding to the transmission destination display device among the overlay images generated in advance.

The term "processor" used in the above description means, for example, circuitry such as a CPU (Central Processing Unit), a GPU (Graphics Processing Unit), an ASIC (Application Specific Integrated Circuit), or a programmable logic device (for example, an SPLD (Simple Programmable Logic Device), a CPLD (Complex Programmable Logic Device), or an FPGA (Field Programmable Gate Array)). Note that the processing circuitry 33 may incorporate the medical information processing programs in the circuitry of the processor directly, instead of saving the programs in the storage 34. In this case, the processor implements a function by reading out the program incorporated in the circuitry and executing it. Note that each processor of the embodiment is not necessarily formed as a processor. A plurality of independent circuitry may be combined to form one processor and implement the function.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

The invention claimed is:

1. A medical image processing apparatus comprising:
 a storage configured to store a first image indicating a breast of an object captured by a medical image diagnostic apparatus and interpretation information associated with the first image; and
 processing circuitry configured to
  generate, based on position information of a region of interest based on the interpretation information and information of an interpretation direction, schematic diagram information for adding information about a position of the region of interest onto a schematic diagram of the breast, and
  transmit information, including the schematic diagram information, for generating the schematic diagram.

2. The apparatus of claim 1, wherein the information about the position of the region of interest includes a line passing through the region of interest.

3. The apparatus of claim 1, wherein the first image is a mammography image acquired by irradiating the breast of the object with X-rays.

4. The apparatus of claim 1, wherein the first image is acquired by tomosynthesis examination in which an X-ray image on an arbitrary slice of the breast of the object can be acquired by reconstructing a plurality of X-ray images captured from multiple directions.

5. A medical image processing apparatus comprising:
 a storage configured to store a first image indicating a breast of an object captured by a medical image diagnostic apparatus and interpretation information associated with the first image; and
 processing circuitry configured to
  determine, based on information about a display, a layout when displaying the first image on the display,
  generate a second image based on the determined layout and the interpretation information associated with the first image, and
 transmit the first image and the second image to the display.

6. The apparatus of claim 5, wherein
 the display is connected via a network, and
 the processing circuitry acquires the information about the display via the network.

7. The apparatus of claim 5, wherein the first image is a mammography image acquired by irradiating the breast of the object with X-rays.

8. The apparatus of claim 5, wherein the first image is acquired by tomosynthesis examination in which an X-ray image on an arbitrary slice of the breast of the object can be acquired by reconstructing a plurality of X-ray images captured from multiple directions.

9. The apparatus of claim 5, wherein if no region of interest is set on the first image, the processing circuitry determines not to generate the second image.

10. The apparatus of claim 5, wherein the processing circuitry determines the layout based on information about a display region on the display.

11. The apparatus of claim 5, wherein the processing circuitry selects, in accordance with a display region on the display, the layout from a first layout in which the interpretation information is displayed outside a region indicating the breast on the first image and a second layout in which the interpretation information is displayed in a different region outside the first image.

12. The apparatus of claim 5, wherein the processing circuitry determines the layout in which a color of at least part of the second image is set to a color different from the first image.

13. The apparatus of claim 5, further comprising:
an input interface configured to accept input information from an operator,
wherein upon accepting, from the operator via the input interface, an input indicating that no abnormal finding is found on the first image, the processing circuitry determines not to transmit the first image to the display.

14. The apparatus of claim 5, further comprising:
an input interface configured to accept input information from an operator,
wherein upon accepting, from the operator via the input interface, an input indicating that no abnormal finding is found on the first image, the processing circuitry determines to transmit the first image to the display by decreasing a data capacity of the first image.

15. The apparatus of claim 5, wherein in a state in which different pieces of information are assigned to the first image and the second image, the processing circuitry stores the first image and the second image in the same DICOM file.

16. The apparatus of claim 5, wherein the processing circuitry stores the interpretation information as addition information in a DICOM file corresponding to the first image.

17. The apparatus of claim 5, wherein the processing circuitry generates a composite image by compositing a plurality of first images, and generates the second image corresponding to the composite image.

18. The apparatus of claim 17, wherein in a state in which different pieces of information are assigned to the composite image and the second image, the processing circuitry stores the composite image and the second image in the same DICOM file.

19. The apparatus of claim 5, wherein the interpretation information includes at least one of a schematic diagram corresponding to an imaging direction of the first image, a finding comment for the first image indicating the breast of the object, and a graphic indicating a region of interest set on the first image.

20. A medical image processing apparatus comprising:
storage configured to store a first image of a breast of an object captured by a medical image diagnostic apparatus, interpretation information about the first image, and layouts of a plurality of display screens;
an input interface configured to accept input information from an operator; and
processing circuitry configured to
load the first image and the interpretation information from the storage, and determine a layout of a second image corresponding to the plurality of display screens,
generate the second image based on the layout, and output the second image to the storage, and
accept the input information from the input interface, read out the second image from the storage, and transmit the readout second image to the display screen together with the first image.

21. A non-transitory computer-readable storage medium comprising a program used by a computer, the program causing the computer to execute:
processing of loading, from storage, interpretation information about a first image of a breast of an object captured by a medical image diagnostic apparatus;
processing of generating, based on position information of a region of interest based on the interpretation information and information of an interpretation direction, schematic diagram information for adding information about a position of the region of interest onto a schematic diagram of the breast; and
processing of transmitting information, including the schematic diagram information, for generating the schematic diagram.

* * * * *